United States Patent [19]

Wiedemann

[11] Patent Number: 4,830,764
[45] Date of Patent: May 16, 1989

[54] POLYOXYALKYLENE-CONTAINING PHOSPHORIC ACID ESTERS

[75] Inventor: Achim Wiedemann, Weil am Rhein, Fed. Rep. of Germany

[73] Assignee: Sandoz Ltd., Basel, Switzerland

[21] Appl. No.: 112,790

[22] Filed: Oct. 23, 1987

[30] Foreign Application Priority Data

Oct. 27, 1986 [DE] Fed. Rep. of Germany ....... 3636543

[51] Int. Cl.$^4$ .............................................. D06M 1/00
[52] U.S. Cl. ..................................... 252/8.6; 558/186; 252/DIG. 17; 252/174.16
[58] Field of Search ........................... 558/186; 252/8.6

[56] References Cited

U.S. PATENT DOCUMENTS 3,619,274 11/1971 Proffitt ............................. 117/138.8

FOREIGN PATENT DOCUMENTS

| 0197001 | 3/1986 | European Pat. Off. . |
|---|---|---|
| 1081285 | 8/1967 | United Kingdom . |
| 1286699 | 8/1972 | United Kingdom . |
| 1356361 | 6/1974 | United Kingdom . |
| 1402326 | 8/1975 | United Kingdom . |
| 1473222 | 5/1977 | United Kingdom . |
| 2105745 | 3/1983 | United Kingdom . |

*Primary Examiner*—John F. Niebling
*Assistant Examiner*—Isabelle Rodriquez
*Attorney, Agent, or Firm*—Gerald D. Sharkin; Richard E. Vila; Thomas C. Doyle

[57] ABSTRACT

The invention relates to phosphoric acid partial esters derived from a block ethoxylated and propoxylated $C_{9-16}$ aliphatic alcohol. These phosphoric acid partial esters are useful as wetting agents, especially in the pre-treatment of cellulosic textile materials.

13 Claims, No Drawings

POLYOXYALKYLENE-CONTAINING PHOSPHORIC ACID ESTERS

The present invention relates to surface-active agents particularly useful for the pre-treatment of textile materials.

According to the invention, there is provided a compound of formula I

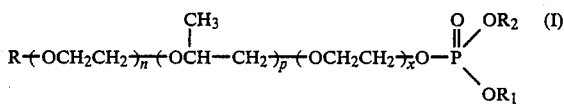

wherein
each R, independently, is linear or branched $C_{9-16}$alkyl or $C_{9-16}$alkenyl;
$R_1$ has one of the significances given for $R_2$ or is a radical of formula

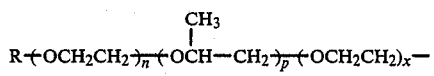

each $R_2$, independently, is hydrogen, alkali metal, ammonium or an equivalent of an alkaline earth metal;
each n, independently, is 0 to 10,
each p, independently, is 1 to 7, and
each x, independently, is 2 to 10
or a mixture of such compounds.

R is preferably R', where R' is linear or branched $C_{9-14}$alkyl, particularly branched $C_{9-13}$alkyl, especially branched $C_{13}$alkyl.

n is preferably n', where n' is a number from 2 to 10. More preferably, n is n", where n" is a number from 2 to 4.

p is preferably p', where p' is a number from 1 to 5. More preferably p is p", where p" is a number from 3 to 5.

x is preferably x', where x' is a number from 2 to 7. More preferably x is x", where x" is a number from 5 to 7.

Preferred alkali metal as $R_2$ is sodium or potassium. Preferably $R_2$ is hydrogen, sodium or potassium, more preferably hydrogen.

Preferred compounds of formula I are those wherein R is R', preferably branched $C_{9-13}$alkyl;
n is n', preferably n";
p is p', preferably p";
x is x', preferably x".

When Formula I has the values n", p" and x", it may be designated Formula I".

Suitable mixtures of compounds of formula I include a mixture of phosphoric acid monoesters or phosphoric acid diesters or a mixture of phosphoric acid monoesters and diesters. These mixtures may comprise compounds having various combinations of significances, e.g. the R's may be a $C_{9-16}$alkyl and $C_{9-16}$alkenyl, the n's, p's and/or x's may respectively be different. Preferred mixtures are those based on a mixture of monoesters with diesters, more preferably a mixture of a monoester with a diester in which the R's, n's, p's and x's are identical.

The compounds of formula I may be produced by conventional methods. Thus, they may be prepared by esterifying the adduct resulting from the ethoxylation and propoxylation (with n moles ethylene oxide, p moles propylene oxide and x moles ethylene oxide, respectively) of an aliphatic $C_{9-16}$alcohol with a phosphating agent, e.g. phosphoric acid or a derivative thereof, for example a polyphosphoric acid, preferably tetraphosphoric acid. The esterification into partial phosphoric esters is advantageously carried out at a temperature from 80° to 100° C.

Preferably the mole ratio of the block oxyethylated-/oxypropylated $C_{9-16}$alcohol to the phosphating agent, for example tetraphosphoric acid, is 3–20:1, more preferably 3–12:1.

The alkoxylation step is preferably carried out in the presence of a conventional catalyst, for example an alkali metal hydroxide.

When compounds of formula I in which n is other than 0 are prepared, an amount of ethylene oxide calculated to provide the desired degree of the first ethoxylation is introduced and the resulting mixture is allowed to react until the ethylene oxide is consumed, as indicated by the reaction pressure no longer decreasing with time. A similar introduction and reaction of a calculated amount of propylene oxide serves to provide either the second block (n≠0) or the first block (n=0). A further introduction and reaction of a calculated amount of ethylene oxide serves to complete the alkoxylation. It should be understood that each separate alkoxylation procedure serves to introduce a desired average number of alkylene oxide units per alcohol molecule. In each block the values of n, p and x as average values may be other than whole numbers.

The partial esters of formula I are preferably used as resulting from the esterification reaction, e.g. in the acid form ($R_2$=H), particularly as a mixture of mono- and diesters. Preferred mono-/di-ester mixtures are those in which the monoester predominates, for example those in which the weight ratio of monoester to diester is from 3–20:1, particularly 3–12:1. If desired, the compounds of formula I in which $R_2$ is H can be converted by conventional methods into compounds in which $R_2$ is an alkali metal, ammonium or an equivalent of an alkaline earth metal ion.

The compounds of formula I, are useful surface-active agents. They are advantageously used in the form of an aqueous composition, preferably as a composition comprising from 20 to 70% by weight (based on the total weight) of phosphoric acid partial ester(s) of formula I.

Preferred compositions of the invention are aqueous compositions comprising from 25 to 55% by weight of a compounds of formula I or a mixture of such compounds, particularly from 35 to 40% by weight, based on the total weight of the composition.

According to a further preferred embodiment of the invention, the composition comprises, in addition to the 20–70% by weight of the compound(s) of formula I, (i) from 1 to 5% by weight of an aliphatic $C_{9-18}$alcohol, or (ii) from 1 to 8% by weight of a solubilising agent or a mixture of components (i) and (ii), the balance to 100% by weight being water.

Component (i) is preferably a branched $C_{9-18}$alkanol. Component (i) may also be a mixture of aliphatic alcohols.

Component (ii) is preferably a solubilising agent of the glycol ether series, for example a mono- or di-($C_{2-3}$alkylene)glycol mono-($C_{1-4}$alkyl)ether, preferably a di-($C_{2-3}$alkylene)glycol mono-($C_{1-4}$alkyl)ether.

The compositions of the invention are useful surfactants, particularly wetting agents for textiles. They are more particularly suitable for use in an aqueous treatment of cellulosic material, preferably pre-treatments where it is desired to obtain a rapid and effective wetting of the material to be pre-treated, e.g. pre-washing, alkaline scouring, enzymatic desizing, cold or warm peroxide bleaching or hypochlorite or chlorite bleaching. The compositions of the invention have good wetting properties at acid, neutral or alkaline pH values and thus contribute to improve the treatment carried out in their presence; they are preferably used at a pH ranging from pH4 to 16° Bé NaOH. In addition to their wetting properties, the compositions of the invention have a good washing and dispersing power, particularly on cotton impurities, and a good defatting action. They are compatible with enzymes, particularly desizing enzymes, and exhibit a good stability in bleaching liquors based on hydrogen peroxide, sodium hypochlorite or sodium chlorite. With the compositions of the invention, foam formation is kept to a minimum.

The optimum amount of composition to be used may vary depending on the compounds of formula I used, the desired effect etc. Preferably the compositions of the invention are used in an amount of from 4 to 6 g per liter treatment bath based on a composition containing from 35 to 40% by weight of a compound of formula I, which corresponds to a concentration of about 0.15 to 0.23% by weight of compound of formula I in the treatment bath. More preferably, the compositions of the invention are used in a concentration such that 0.06 to 0.5% by weight of compound of formula I based on the dry weight of the textile material is absorbed on the textile material at the end of the treatment.

Furthermore, the present invention provides also a process for treating a cellulosic textile material comprising a wetting step, which process comprises bringing into contact the textile material with an effective amount of a compound of formula I or a mixture of such compounds, preferably in the form of an aqueous composition.

As already mentioned, the composition is preferably applied for improving the wetting of a cellulosic textile material in the pretreating of such material. The process of the invention may be carried out according to known methods, e.g. by a discontinuous, semi-continuous or continuous method, preferably semi-continuously or continuously. The textile material is preferably impregnated with the treatment bath containing the pretreating agents and the wetting composition, e.g. by padding, immersion or spraying, and then the impregnated material is allowed to dwell or is submitted to a heat treatment e.g. as is conventional in a bleaching, scouring or desizing treatment.

By "cellulosic" material is to be understood a textile material comprising natural or regenerated cellulosic fibres, e.g. cotton, rayon or viscose, linen, hemp or jute, and their blends with further natural or synthetic fibres, e.g. polyester. The term "material" is used broadly to cover all stages of manufacture including yarns, bobbins, woven, knitted or non-woven goods. Cotton and cotton/polyester blends are particularly preferred.

The following Examples in which all parts are by weight and all temperatures are in degrees Centigrade, illustrate the invention without any limitation of the scope.

EXAMPLE 1

(a) Preparation of the phosphoric acid partial esters

705 Parts of a block polymer obtained by reacting isotridecyl alcohol with ethylene oxide, propylene oxide and ethylene oxide in the mole ratio of 1:2:4:7, are stirred with 36 parts tetraphosphoric acid for 8 hours at 85°–90°. There is obtained an acidic mixture of phosphoric acid esters which gives a pH value of 2.4 after dilution with water to a 1% aqueous solution.

(b) Composition

38 Parts of the acidic mixture of phosphoric acid esters obtained above are mixed at 40° in the following sequence with
  1 part isotridecanol
  1 part isodecanol
  5 parts diethyleneglycol monobutyl ether
  2.5 parts 30% NaOH, and
  52.5 parts demineralized water
until homogeneous. The resulting composition has a pH value of 4.1.

EXAMPLES 2 TO 57

By following the procedure of Example 1 but replacing the 705 parts of isotridecyl block polymer by an appropriate amount of the block polymers indicated in the following Table, further phosphoric acid partial esters of the invention can be prepared.

TABLE 1

| Ex. | R | n | p | x |
|---|---|---|---|---|
| 2 | iso-$C_{13}$Alkyl | 0 | 2 | 7 |
| 3 | " | 7 | 4 | 4 |
| 4 | n-$C_{9-11}$Alkyl | 0 | 4 | 4 |
| 5 | iso-$C_{10}$Alkyl | 4 | 4 | 4 |
| 6 | " | 4 | 1 | 4 |
| 7 | " | 7 | 4 | 7 |
| 8 | iso-$C_{13}$Alkyl | 7 | 4 | 7 |
| 9 | " | 0 | 1 | 2 |
| 10 | " | 0 | 1 | 4 |
| 11 | " | 0 | 1 | 7 |
| 12 | " | 2 | 1 | 2 |
| 13 | " | 2 | 1 | 4 |
| 14 | " | 2 | 1 | 7 |
| 15 | " | 4 | 1 | 2 |
| 16 | " | 4 | 1 | 4 |
| 17 | " | 4 | 1 | 7 |
| 18 | " | 7 | 1 | 2 |
| 19 | " | 7 | 1 | 4 |
| 20 | " | 7 | 1 | 7 |
| 21 | " | 0 | 2 | 2 |
| 22 | " | 0 | 2 | 4 |
| 23 | " | 2 | 2 | 2 |
| 24 | " | 2 | 2 | 4 |
| 25 | " | 2 | 2 | 7 |
| 26 | " | 4 | 2 | 2 |
| 27 | " | 4 | 2 | 4 |
| 28 | " | 4 | 2 | 7 |
| 29 | " | 7 | 2 | 2 |
| 30 | " | 7 | 2 | 4 |
| 31 | " | 7 | 2 | 7 |
| 32 | iso-$C_{13}$Alkyl | 0 | 4 | 2 |
| 33 | " | 0 | 4 | 4 |
| 34 | " | 0 | 4 | 7 |
| 35 | " | 2 | 4 | 2 |
| 36 | " | 2 | 4 | 4 |
| 37 | " | 4 | 4 | 2 |
| 38 | " | 4 | 4 | 4 |
| 39 | " | 4 | 4 | 7 |
| 40 | " | 7 | 4 | 2 |
| 41 | $C_{9-11}$-Alkyl | 2 | 4 | 2 |
| 42 | " | 2 | 4 | 4 |
| 43 | " | 2 | 4 | 7 |
| 44 | " | 4 | 4 | 2 |
| 45 | " | 4 | 4 | 4 |

TABLE 1-continued

| Ex. | R | n | p | x |
|---|---|---|---|---|
| 46 | " | 4 | 4 | 7 |
| 47 | " | 7 | 4 | 2 |
| 48 | C$_{9-11}$-Alkyl | 7 | 4 | 4 |
| 49 | " | 7 | 4 | 7 |
| 50 | iso-C$_{10}$Alkyl | 0 | 2 | 2 |
| 51 | " | 7 | 2 | 4 |
| 52 | " | 0 | 4 | 2 |
| 53 | " | 0 | 4 | 4 |
| 54 | " | 0 | 4 | 7 |
| 55 | " | 2 | 4 | 4 |
| 56 | " | 2 | 4 | 7 |
| 57 | " | 4 | 4 | 7 |

Application Example A: Enzymatic Desizing

A starch sized raw cotton fabric is impregnated at 70° with an aqueous bath containing, per 1000 parts,
  5 parts of the composition of Example 1
  4 parts of a commercially available bacterial amylase (e.g. Bactolase 400% from Schweiz. Ferment AG, Switzerland), and
  5 parts sodium chloride
to a pick-up of 85% based on the dry weight. The impregnated fabric is rolled and stored for 4 to 24 hours. The fabric is then rinsed with hot, warm and then cold water. An optimal degradation of the starch size is obtained without any disturbing foaming.

By following the above procedure, a sized 50:50 polyester/cotton fabric is desized with good results.

Application Example B: Cold Peroxide Bleaching

A bleaching bath of 900 l containing
  2.5 kg of the composition of Example 1,
  0.2 kg of magnesium sulphate heptahydrate,
  8.0 kg waterglass,
  45 l of 50% sodium hydroxide solution,
  7.0 kg of sodium persulphate, and
  36 l of 50% hydrogenperoxide
is prepared in a container. An unbleached cotton fabric is immersed at 20° in this bath, squeezed between two padding rollers to a pick-up of 80% based on the dry weight, rolled, wrapped in a plastic sheet and dwelt for 16 hours. The bath is continuously completed from the preparing container through regulation means of the level. The bleached fabric is then washed warm.

A good bleaching effect is obtained in the absence of any undesirable foaming during the bleaching treatment.

By following the above procedure, an unbleached 50:50 polyester/cotton mixed fabric is bleached with good results.

Application Example C: Alkaline Scouring

A raw cotton fabric is impregnated at 60° according to a continuous process with an aqueous bath containing, per 1000 parts, 60 parts caustic soda and 6 parts of the composition of Example 1, to a pick-up of 85% based on the dry weight. Thereafter the fabric is steamed for 70 seconds at a temperature of 103° and then rinsed warm and cold. During impregnation, the scouring bath is completed with a stock solution containing 32 parts per 1000 parts of the composition of Example 1.

A good scouring effect is obtained without any disturbing foaming during the treatment.

A raw 50:50 polyester/cotton mixed fabric is scoured with good results when treated according to the above procedure.

The compositions of Examples 2 to 57 can be used instead of the composition of Example 1 in the above application examples A, B and C. Good results are obtained.

After drying, the fabric treated according to Application Example C with any one of the compositions of Examples 1 to 57 exhibits a good absorbing power.

What is claimed is:

1. An aqueous composition containing 20 to 70% by weight of a compound or mixture of compounds represented by the following formula:

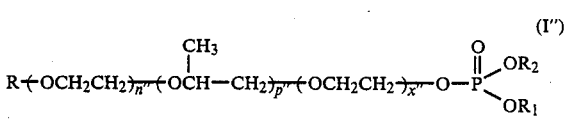

wherein
  each R, independently, is linear or branched C$_{9-16}$alkyl or C$_{9-16}$alkenyl;
  R$_1$ has one of the significances given for R$_2$ or is a radical of formula

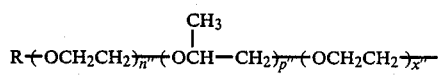

each R$_2$, independently, is hydrogen, alkali metal, ammonium or an equivalent of an alkaline earth metal;
  each n", independently, is a number from 2 to 4;
  each p", independently, is a number from 3 to 5;
  each x", independently, is a number from 5 to 7;
said composition being useful for the treatment of such compounds.

2. An aqueous composition according to claim 1, wherein R is branched C$_{9-13}$alkyl.

3. A composition according to claim 1 containing in addition
  (i) from 1 to 5% by weight of an aliphatic C$_{9-18}$ alcohol, or
  (ii) from 1 to 8% by weight of a solubilising agent or a mixture of components (i) and (ii), the balance to 100% by weight being water.

4. A composition according to claim 2 containing in addition
  (i) from 1 to 5% by weight of an aliphatic C$_{9-18}$ alcohol, or
  (ii) from 1 to 8% by weight of a solubilising agent or a mixture of components (i) and (ii), the balance to 100% by weight being water.

5. A composition according to claim 3 wherein component (ii) is a glycol ether.

6. A composition according to claim 4 wherein component (ii) is a glycol ether.

7. A composition according to claim 4 wherein component (i) is a branched C$_{9-18}$alkanol and component (ii) is a mono- or di-(C$_{2-3}$alkylene)glycol mono-(C$_{1-4}$alkyl)ether.

8. A process for treating a cellulosic textile material comprising a wetting step, which process comprises bringing into contact the textile material with an effective amount of a compound or a mixture of compounds of the formula

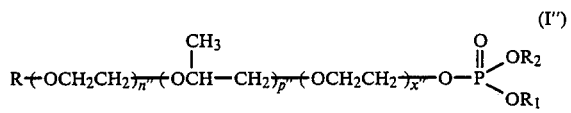

(I")

wherein
  each R, independently, is linear or branched $C_{9-16}$alkyl or $C_{9-16}$alkenyl;
  $R_1$ has one of the significances given for $R_2$ or is a radical of formula

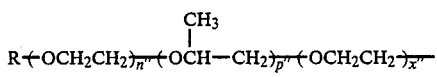

each $R_2$, independently, is hydrogen, alkali metal, ammonium or an equivalent of an alkaline earth metal;
  each n", independently, is a number from 2 to 4,
  each p", independently, is a number from 3 to 5,
  each x", independently, is a number from 5 to 7.

9. A process according to claim 8 wherein, in Formula I", R is branched $C_{9-13}$alkyl.

10. A process according to claim 9 in which the treatment is a continuous or semi-continuous pretreatment.

11. In a process wherein a cellulosic textile material is pretreated in an aqueous bath containing a wetting agent, the improvement which comprises employing as the wetting agent an amount of a compound or mixture of compounds of the formula

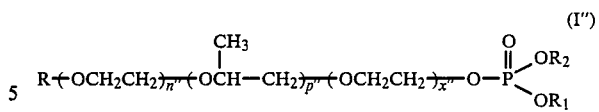

(I")

wherein
  each R, independently, is branched $C_{9-13}$alkyl;
  $R_1$ has one of the significances given for $R_2$ or is a radical of formula

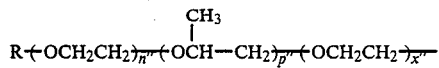

each $R_2$, independently, is hydrogen, alkali metal, ammonium or an equivalent of an alkaline earth metal;
  each n", independently, is a number from 2 to 4,
  each p", independently, is a number from 3 to 5,
  each x", independently, is a number from 5 to 7,
said amount being effective to improve the wetting of said material.

12. A process according to claim 11 wherein the aqueous pretreatment bath contains an amount of a compound or mixture of compounds of Formula I" such that 0.06 to 0.5% by weight thereof, based on the dry weight of the textile material, is absorbed on the textile material.

13. A process according to claim 11 wherein the pretreatment is a pre-washing, alkaline scouring, enzymatic desizing, cold or warm peroxide bleaching or hypochlorite or chlorite bleaching.

* * * * *

UNITED STATES PATENT AND TRADEMARK OFFICE
CERTIFICATE OF CORRECTION

PATENT NO. : 4,830,764

DATED : May 16, 1989

INVENTOR(S) : Achim Wiedemann

It is certified that error appears in the above-identified patent and that said Letters Patent is hereby corrected as shown below:

Column 6, Claim 1, last two lines; change "treatment of such compounds" to -- pretreatment of textiles --.

Signed and Sealed this

Twenty-sixth Day of December, 1989

*Attest:*

JEFFREY M. SAMUELS

*Attesting Officer*     *Acting Commissioner of Patents and Trademarks*